(12) United States Patent
Johnson

(10) Patent No.: US 6,414,330 B1
(45) Date of Patent: Jul. 2, 2002

(54) METHOD AND APPARATUS FOR APPLYING ELECTRON RADIATION TO SUBCUTANEOUS CELLS

(76) Inventor: Jim H. Johnson, 44B Kirk Ave., San Jose, CA (US) 95127

( * ) Notice: Subject to any disclaimer, the term of this patent is extended or adjusted under 35 U.S.C. 154(b) by 0 days.

(21) Appl. No.: 09/326,114

(22) Filed: Jun. 4, 1999

(51) Int. Cl.[7] ................................................. A61N 5/00
(52) U.S. Cl. ............................ 250/492.3; 600/1; 600/3
(58) Field of Search ......................... 280/492.1–492.3; 600/1, 3; 250/492.3

(56) References Cited

U.S. PATENT DOCUMENTS

| | | | |
|---|---|---|---|
| 4,760,265 A | * 7/1988 | Yoshida et al. | 250/492.2 |
| 5,073,913 A | 12/1991 | Martin | |
| 5,144,647 A | 9/1992 | Kikuchi | |
| 5,190,516 A | * 3/1993 | Bronn | 600/1 |
| 5,216,255 A | * 6/1993 | Weidlich | 250/492.3 |
| 5,360,666 A | 11/1994 | Eichmiller | |
| 5,585,643 A | * 12/1996 | Johnson | 250/492.3 |

OTHER PUBLICATIONS

W. E. Dance, D. H. Rester, B. J. Farmer, J. H. Johnson & L. L. Baggerly, "Bremsstrahlung Produced in Thick Aluminum & Iron Targets by 0.5 to 2.8 MeV Electrons", Journal of Applied Physics, May 1968, vol. 39, No. 6, pp. 2881–2889.

D. H. Rester and W. E. Dance, Bremsstrahlung Cross–Section Measurements at Incident Electron Energies of 1.0, 1.7, and 2.5 MeV, Physical Review, Sep. 5, 1967, vol. 161, No. 1, pp. 85–93.

D. H. Rester and W. E. Dance, "K–Shell Ionization of Ag, Sn, and Au from Electron Bombardment", Physical Review, Second Series, Dec. 2, 1966, vol. 152, No. 1, pp. 1–3.

* cited by examiner

*Primary Examiner*—Kiet T. Nguyen
*Assistant Examiner*—David A. Vanore
(74) *Attorney, Agent, or Firm*—Stanley Z Cole; Edward Berkowitz

(57) ABSTRACT

Uniform electron irradiation of tissue over a large solid angle is accomplished by directing an electron beam of selectively variable energy and intensity through a hollow needle to emerge in the interior of a tissue equivalent scattering body adapted for insertion into a surgical opening. Multiple scattering of electrons in the interior of the scattering body produces a flux emerging from the surface of the body, which flux exhibits a desired distribution of intensity and kinetic energy (depth of penetration) over a large solid angle interval for radiation treatment of surrounding tissue.

7 Claims, 3 Drawing Sheets

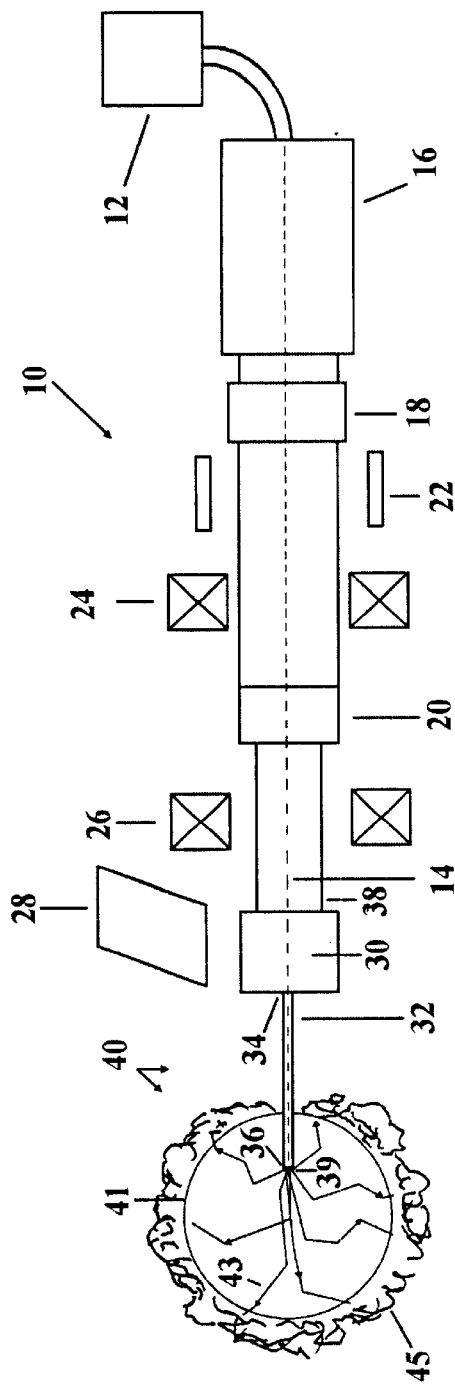
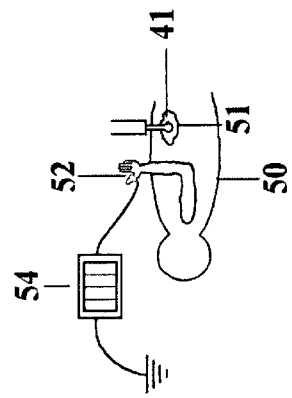
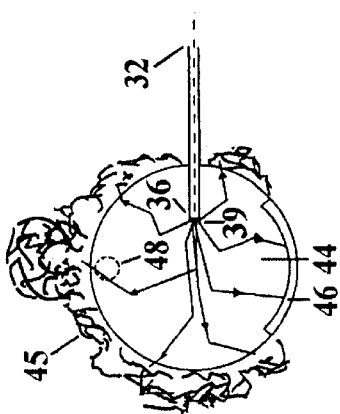

METHOD AND APPARATUS FOR APPLYING ELECTRON RADIATION TO SUBCUTANEOUS CELLS

FIELD OF THE INVENTION

The invention relates generally to radiation therapy for in vivo treatment of malignant cells in humans and animals, and more particularly to the method and apparatus for selective application of the electron flux to tissue with minimal damage to healthy tissue.

BACKGROUND OF THE INVENTION

Radiation therapy is commonly understood to comprehend the application of ionizing radiation to a body for the purpose of damaging malignant tissue. The typical example is the use of bremmstrahlung X-rays from an electron accelerator or the collimated ray photons from a radiaoactive source, such as $^{60}$Co. All tissue in the path of such a radiation beam are exposed to the effects of the ionizing radiation. These energetic photons are highly penetrating and may interact with the tissue through which they pass on a statistical basis. There is a probability for a particular interaction depending upon the photon energy and the nature of the material (tissue) through which they pass. The most likely interactions for electron energies greater than about 1 KeV, include the Compton effect, and above a photon energy of 1.2 MeV, pair production. These interactions may be regarded as mechanisms whereby energetic electrons (and, for pair production, also positrons) are produced at the site of the interaction. Often, lower energy photon(s) are also produced and these proceed further into the tissue, in somewhat different direction from the original photon direction, and the process proceeds, on a probabalistic basis for individual electron scattering events. That is, a photon flux emerges from the exit surface of the body which differs somewhat from the character of the photon flux on the entry surface. This simply reflects that the likelihood of interaction is small for photons transiting tissue in comparison with material of high atomic number, such as lead. The effect of that portion of the photon flux which does interact in the path directed through tissue is substantial due to the damage done to cells by the energetic electrons resulting from photon scattering and absorption processes. Such damage is suffered alike by healthy and malignant cells, but malignant cells are typically more sensitive to radiation than are healthy cells. Much effort has been directed to reducing the damage done to healthy tissue.

Direct utilization of electron fluxes is also known. Electrons are available from radioactive sources (-emitters) or as controllable energetic, focussed beams from accelerator sources. Radioactive sources present hazards in handling, and emission therefrom, is uncontrolled in direction, energy and intensity. In any use of direct electron treatment, it must be recognized that electrons lose energy in traversing any path through matter. In contrast with the interaction of photons in passing through matter, the likelihood is very high for interaction by electrons with the environment through which they pass. The mechanisms need not be discussed here other than to recognize that as a result of such interaction, the electron loses energy and momentum to its environs in collision with atoms, and it continues on a trajectory which differs in angle and energy (a scattering event) where the differences depend upon the initial energy of the electron and the nature of the environment (the specific character of atoms encountered in such trajectory).

In the prior art, there is described method and apparatus for directing an electron beam through a hollow needle to scatter from a metallic disk affixed to the distal end of the needle. As described, an electron beam of several MeV energy scatters from a foil of aluminum, titanium or heavier metal which may, in a typical case have a thickness in the range 0.002 to 0.038 inches. This thickness can be greater however, provided that it is less than the range of the incident electrons in the material being used. The scattered electrons then emerge to fill a treatment volume defined by the therapy. In practice, this arrangement provides a somewhat diffuse point source of electrons having an angular distribution which, in general, is peaked in the forward direction. The angular distribution may be made almost spherical through proper choice of incident energy, scattering material and material thickness. This is described further in U.S. Pat. No. 5,585,643 to the present inventor and incorporated herein by reference. This prior art was directed to treatment of subcutaneous tissue, principally through needle insertion procedures.

When irradiating the site of a malignancy directly with electron radiation, it is desirable to obtain a uniform treatment over the tissue to be treated. In the context of the present invention, a surgical procedure has usually been performed to excise diseased tissue and it is desired to treat a thin layer of surrounding tissue by irradiation. In practice, the dimensions of the tissue area under treatment is many times the dimensions of the typical needle (18 gauge) as described in the prior art.

The need remains for an improved uniform areal density of electrons having substantially uniform spectral properties for impinging the tissue under treatment, together with ability to treat such larger area uniformly and rapidly.

SUMMARY OF THE INVENTION

The present invention provides for directing an energetic electron beam through a hollow needle to scatter from a high Z material to produce a relatively spherical distribution of electrons as disclosed in the prior U.S. Pat. No. 5,585,643. In the present invention, the needle is surrounded by a scattering body (or sphere) of typically low atomic number. The scattering body is preferably a tissue equivalent material which provides for multiple scattering of electrons. These multiply scattered electrons emerge from the surface of the scattering body as a shell of electrons, having effectively absorbed the core of radiation from the quasi-point source of the prior art. The electron flux emerging from the surface of a (homogeneous) scattering body is substantially isotropic and homogeneous in energy. Inhomogeneities may be incorporated into the scattering body to obtain desired anisotropies and energy distributions.

In another aspect of the invention, the patient under treatment is supported in an electrically insulated manner and the charge deposited thereupon is measured through electrical connection from the patient through a charge integrator or a picoammeter to ground for charge integration, whereby the total radiation density encountered is quantitatively known and the dosage to any tissue treated is known from the measured dose distribution data.

BRIEF DESCRIPTION OF THE DRAWINGS

FIG. 1 schematically illustrates an embodiment of the present invention for treating surrounding tissue.

FIG. 2 shows another embodiment of the applicator of the present invention.

FIG. 5 illustrates a method for measuring the radiation dose where the charged particles are completely absorbed by the irradiated body.

DETAILED DESCRIPTION OF THE INVENTION

Figure 3:
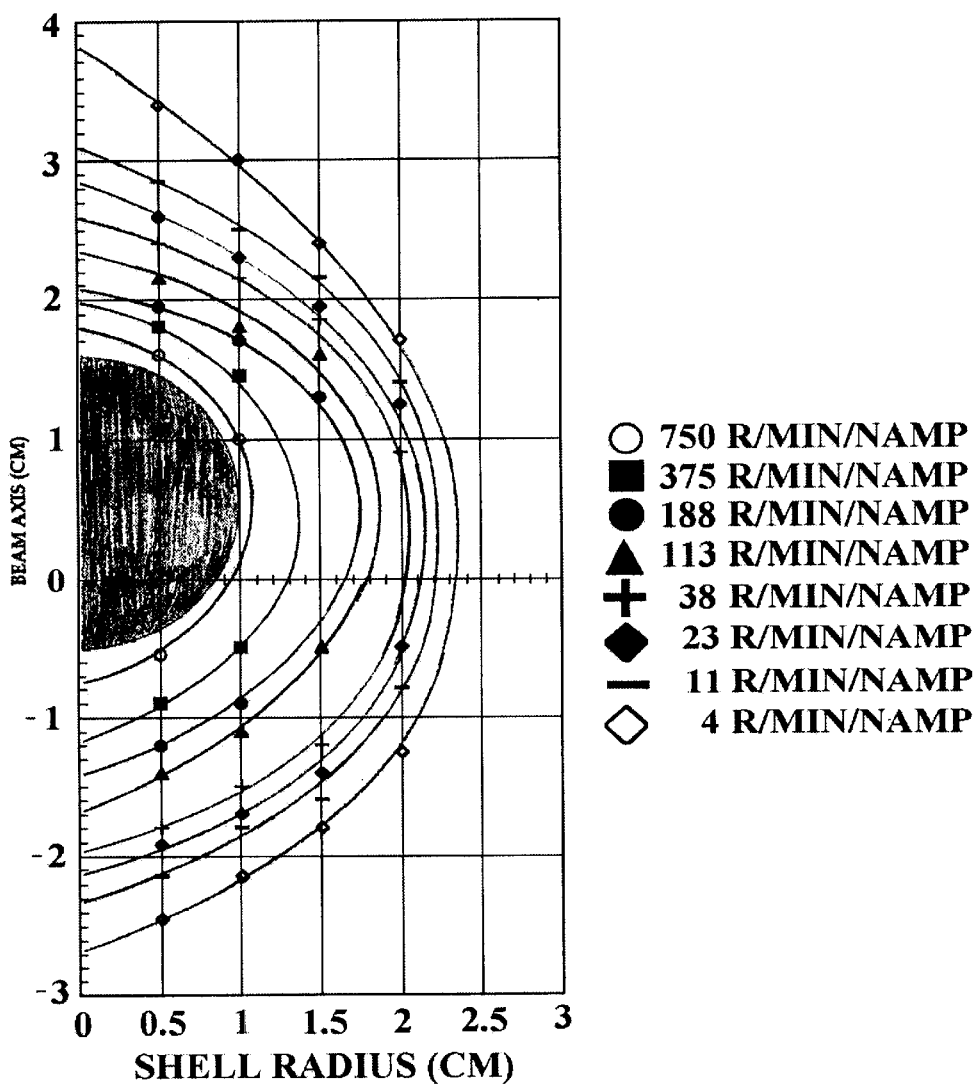
FIG. 3 is figure of revolution about the beam axis showing the entire 4" isodose contours for one realization of the invention.

Turning now to FIG. 1, there is shown a schematic view of the system 10 for providing radiation treatment directly to tissue such as commonly encountered in the context of a surgical wound following removal of malignant tissue. The system 10 includes a source 12 of energetic electrons forming a beam 14 having selectively variable current and kinetic energy effective for electron radiation treatment controlled by a linear accelerator 16. Included in the system 10 are a collimator 18 for defining the lateral dimension of the electron beam. Such beam diameter is typically and preferably about 0.040 inches. A suitable means for collimating the electrons includes an absorber material having a small diameter aperture on the axis of the beam 14. More than one collimator, such as 20, is frequently employed to obtain further effect, such as the elimination of a penumbra from primary slit scattering. Because of the energy and current (power) deposited in the absorber material, the collimator often employs a cooling means to remove heat.

The system 10 in its preferred embodiment also includes electron optical elements as represented by focusing lens 22, and at least one set of steering coils 24 for steering the beam 14. Quadrupole magnet elements are a suitable means for implementing the lens 22. A suitable means for steering the beam are an orthogonal set of coils for directing a uniform magnetic field through a limited region to impart a curved trajectory to the beam in the limited uniform field region. Both X and Y steering may be used to precisely position the beam. A second set of steering coils may be provided to effect a dogleg trajectory in order to direct the beam to transit the bore of needle 32. Needle 32 has proximal end 34 and distal end 36. The proximal end 34 is adapted to mount to the end of the accelerator beam tube 38 and receives the beam 14 therethrough. A suitable means for mounting the proximal end of the needle 32 to the beam tube is a heliarc weld.

Although the device described makes use of a focusing system to control the beam, it should also be understood that this invention will apply and be effective with an accelerator that requires no focusing or aligning.

The system also includes a video camera 28 for observing the glow of the beam as it strikes a lead phosphide screen 30 or other means for visually locating the beam. This visualization of the beam is monitored by the video camera 28 to assist in steering the beam.

At the distal end of the needle 32, the scattering target assembly 40 is mounted. The scattering target assembly preferably includes a high Z material forming a relatively thin foil target/closure member 39 sealing the end of needle 32. The closure member 39 is surrounded by scattering body 41 comprising preferably a low Z material which (for calculational convenience) may be a tissue equivalent material. The target 39, of high Z material, is joined to the scattering body 41 with the distal end of the needle extending to a selected distance into the interior of the scattering body. The distal end of the needle 32 is directed toward the center of the scattering target. The needle is preferably displaced from the center of the scattering mass. The amount of the displacement permits the effective center of the radiation dose angular distribution to appear with desired symmetry in respect to scattering body 41. This arrangement allows a substantial portion of the scattered flux of electrons (fancifully represented by radiation cloud 45) to emerge in the rear angular region.

Representative fanciful trajectories 43 are illustrative of the mechanism. The high Z target 39 is selected to yield a substantial flux of scattered electrons into the rear hemisphere. In the present invention, the interposition of a scattering body 41 diffuses and averages a multiple scattered electron flux over the outer surface thereof. The electrons emitted from the scattering body 41 have the character of a substantially uniform energy range, uniformly distributed over a virtual shell about the surface of scattering body 41. Moreover, the flux of electrons emerging at the surface of the scattering body 41 have the character of an areal distributed source in contrast to a source diverging from point source at target 39.

The electron radiation of the present invention is necessarily accompanied by bremmstrahlung from the high Z target 39. The amount of such extraneous radiation has been found to be less than the background accompanying operation of the accelerator with a 5 MeV beam for a tungsten tipped needle within a 2 cm. tissue equivalent plastic phantom. Bremmstrahlung production is small because the target/scatterer is typically thin to the electron energy, ie. the electron energy loss in the target 39 is small compared to the total electron kinetic energy.

In one example of the invention, the scattering body comprised a solid plastic sphere of radius 1 cm. Supported on an 18 gauge hollow needle terminating about 0.5 cm from the center of the sphere. The scattering body 41 dimensions are chosen such that the electron radiation issuing from the virtual shell of the scattering body surface will exhibit the desired range in tissue under treatment without damage to deeper lying cells.

Turning now to FIG. 2, there is shown another embodiment of the applicator of the present invention which differs from the applicator/scattering target assembly 40 in the use of a composite scattering body 44 which includes a shielding portion 46 for protecting selected regions of solid angle from emission of electrons. The interior portion of the scattering body adjacent the shielding material reduces electron energy significantly while the thickness of the shielding portion 46 may be selected for thickness and composition which yield desired electron energy attenuation or absorption.

Although FIGS. 1 and 2 illustrate spherical scattering bodies, the scattering body shape may be adapted to requirements of the irradiated volume. Moreover, the shape and composition of the scattering target may be designed to produce regions of electron energy and intensity which are enhanced, such as may be obtained by designing a void 48 in the scattering body 41 wherein energy is not lost to passage through the material of the scattering body 41 in emerging through selected solid angle regions.

Figure 4:
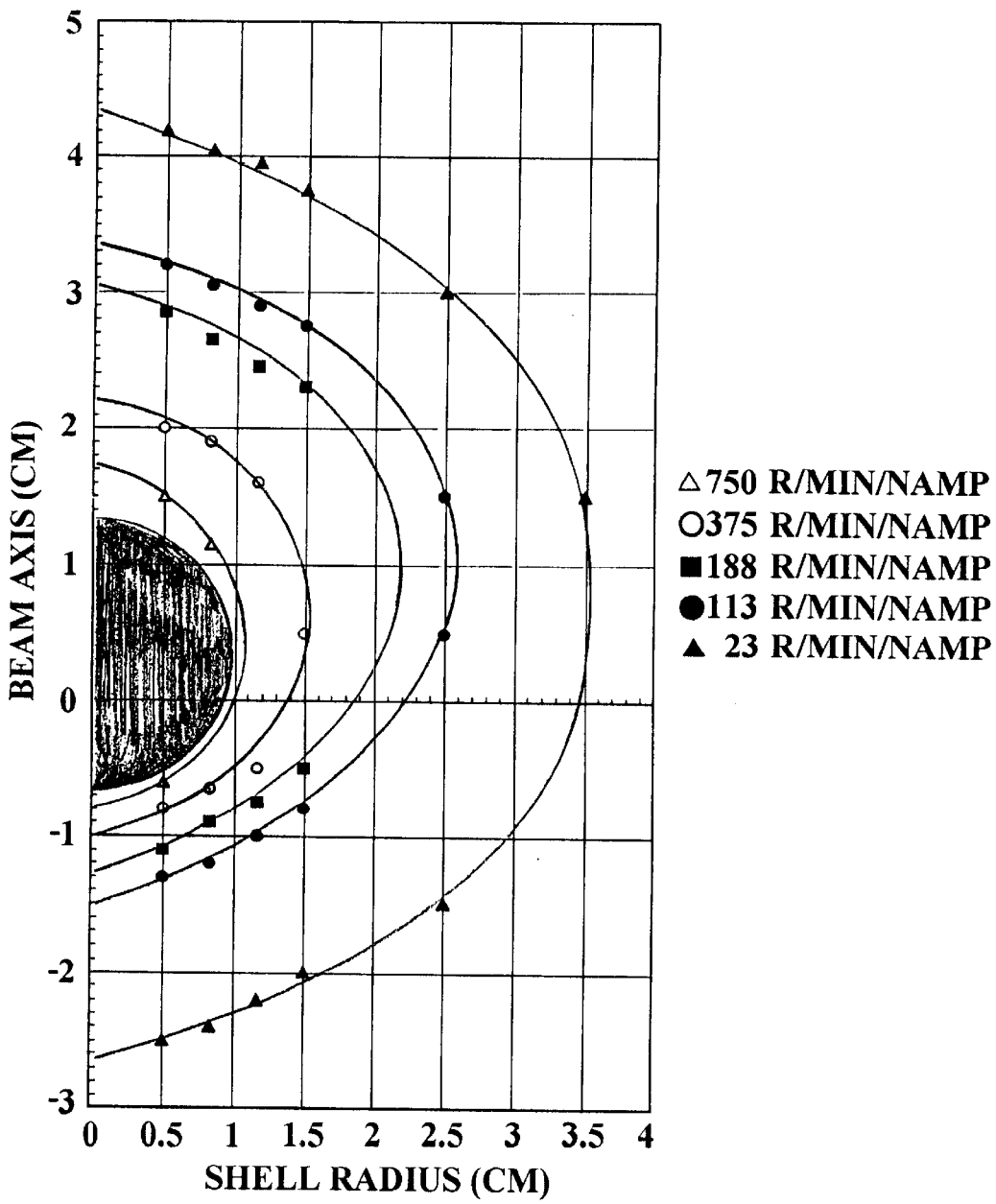
FIG. 4 shows the isodose contours for a higher energy realization of the invention.

FIGS. 3 and 4 show the measured values for the angular dose distribution with respect to the initial electron beam axis for energies of 5 and 10 MeV respectively. The isodose contours (in rads/minute) clearly indicate that the rear hemisphere contains a substantially equal contribution of radiation dose into the solid angle of the rear hemisphere. Note also that the center of symmetry of the angular distribution (ordinate=0) is displaced from the center of the scattering sphere by about 0.5 cm. as expected for displacement of the tip of the needle from the center of the sphere by 0.55 cm for 5 MeV electrons. In the case of FIG. 4, the displacement of the needle from the scattering body center is 0.35 cm and the beam energy is 10 MeV. For both figures the beam current is 1 nanoamp.

In order to plan/measure actual radiation dose to specific tissue, data such as shown in FIGS. 3 and 4 provide the angular distribution of the dose per unit time. Electrical ground of the accelerator is essentially insulated electrically from the patient by the scattering body 41 or other insulating plastic coating proximate a surgical opening 51 as indicated in FIG. 5. The patient 50 is further insulated from extraneous grounding through any suitable patient support structure and a low impedance connector 52 is applied to an extremity of the patient for connection to an instrument 54 for recording the accumulation of electrical charge. Such connectors are commonly employed, as for example in the practice of cardiography. The instrument comprises a pico-ammeter and corresponding integrator, or the equivalent. The measurement there recorded over the irradiation interval represents the total dose of electron radiation emitted from the scattering body and absorbed by the patient. The tissue which has been irradiated is mapped onto the angular distribution about the scattering body 41 and the dose suffered at any point is determinable at any point on such tissue relative to other specific irradiated tissue for the case wherein the irradiated tissue is static relative to the scattering body 41. Relative motion is treatable by straightforward methods beyond the scope of this work.

Although the present invention has been described in reference to a preferred embodiment thereof, variations and modifications will be apparent to those skilled in the art. The present invention is therefore limited not by the specific disclosure herein, but rather by the following claims.

What is claimed is:

1. A device for delivering a flux of electrons forming an electron beam from a source to provide radiation treatment to subcutaneous cells, the device comprising:

a hollow needle having a proximal end and a distal end for respectively directing the electron beam therethrough, the proximal end for attachment to the source of the electron beam, the distal end comprising a scattering target assembly for the electron beam, the scattering target comprising a closure member disposed at the distal end of the hollow needle in the path of the electron beam emerging from the needle of high Z material formed as a relatively thin foil, said closure member for scattering the electron beam over a very large solid angle, the scattering target assembly further comprising an object of low Z tissue equivalent material disposed over said target assembly and having an outer surface of selected shape and having gross dimensions much greater than the diameter of said needle, said object surrounding said closure member, said object comprising a material for further scattering said electrons and degrading a portion of the energy thereof emanating from said target assembly with substantially homogeneous energy distribution of scattered electrons at the outer surface of said object.

2. The device of claim 1 wherein said electrons emerge into a large solid angle at substantially uniform intensity per unit of said solid angle and said solid angle approaches $4\pi$ steradian.

3. The device of claim 2 wherein said scattering target assembly further comprises a portion for further attenuating the energy and density of electrons directed toward said portion, whereby the surface of a selected solid angle portion of said scattering target substantially shields tissue adjacent thereto from electron radiation.

4. The device of claim 2 wherein said scattering target assembly further comprises a void portion therein for enhancing the energy and density of electrons transiting through said portion and issuing from the surface of a selected solid angle portion of said object in relation to electron radiation emitted from non-selected solid angle portions of said object.

5. The method of measuring the radiation dose deposited in tissue of a patient under treatment by a flux of scattered electrons, comprising, establishing the angular distribution of said dose in tissue equivalent material, electrically insulating said patient from electrical ground, directing a flux of scattered electrons to selected tissue of a patient and absorbing the electron charge therein, electrically connecting said patient to an instrument for measuring the accumulation of electrical charge on said patient and measuring said accumulation, mapping the location of irradiated tissue in accordance with said angular distribution, and computing the traction of total dose represented by said angular distribution.

6. A method for intraoperative treatment of exposed tissue, following removal of diseased tissue, by electron radiation, comprising the steps of (a) directing a beam of electrons of selected energy to a location proximate the tissue to be treated, (b) intercepting said electron beam at said location with a high Z scattering material, and (c) interposing a tissue equivalent scattering material of low Z material between said location and said diseased tissue to degrade the energy entering said high Z material to a desired treatment energy level, the electrons emitted from said low Z scattering material comprising an output energy dose for the tissue to be treated by a uniform source of electron radiation.

7. An electron irradiation application device for modifying the emerging radiation field of an essentially point source of energetic electrons to a shell source for irradiation of resected volumes where diseased tissue has been removed from a patient creating a cavity for irradiation, comprising an essentially point source of energetic electrons, a low Z substantially tissue equivalent material positioned on said point source having an outer surface of a pre-selected shell-like shape with dimensions greater in gross size than the diameter of said essentially point source to surround said source and scatter electrons issuing from said source while degrading the energy of said electrons emanating from said source producing a shell of irradiation for irradiating the walls of a resected volume to a controlled depth.

* * * * *

UNITED STATES PATENT AND TRADEMARK OFFICE
CERTIFICATE OF CORRECTION

PATENT NO. : 6,414,330 B1
DATED : July 2, 2002
INVENTOR(S) : Jim H. Johnson

It is certified that error appears in the above-identified patent and that said Letters Patent is hereby corrected as shown below:

Column 6,
Line 29, change "traction" to -- fraction --.

Signed and Sealed this

Fourteenth Day of January, 2003

JAMES E. ROGAN
*Director of the United States Patent and Trademark Office*